United States Patent
Griffin

(10) Patent No.: US 10,747,023 B2
(45) Date of Patent: Aug. 18, 2020

(54) METHOD OF TREATING MYOPIA PROGRESSIONS

(75) Inventor: Richard A. Griffin, Roswell, GA (US)

(73) Assignee: VISIONEERING TECHNOLOGIES, INC., Alpharetta, GA (US)

(*) Notice: Subject to any disclaimer, the term of this patent is extended or adjusted under 35 U.S.C. 154(b) by 825 days.

(21) Appl. No.: 14/126,056

(22) PCT Filed: Jun. 8, 2012

(86) PCT No.: PCT/US2012/041621
§ 371 (c)(1),
(2), (4) Date: Dec. 13, 2013

(87) PCT Pub. No.: WO2012/173891
PCT Pub. Date: Dec. 20, 2012

(65) Prior Publication Data
US 2014/0111763 A1 Apr. 24, 2014

Related U.S. Application Data

(60) Provisional application No. 61/497,500, filed on Jun. 15, 2011.

(51) Int. Cl.
*G02C 7/06* (2006.01)
*G02C 7/04* (2006.01)
(Continued)

(52) U.S. Cl.
CPC ............ *G02C 7/061* (2013.01); *G02C 7/027* (2013.01); *G02C 7/042* (2013.01); *G02C 7/044* (2013.01);
(Continued)

(58) Field of Classification Search
CPC ........ G02B 2202/24; G02C 7/41; G02C 7/42; G02C 7/44
(Continued)

(56) References Cited

U.S. PATENT DOCUMENTS

| 5,225,858 A | 7/1993 | Portney |
| 5,526,071 A | 6/1996 | Seidner |

(Continued)

FOREIGN PATENT DOCUMENTS

| CN | 1582408 A | 2/2005 |
| CN | 101541271 A | 9/2009 |

(Continued)

OTHER PUBLICATIONS

Smith III, E.L., et al; "Peripheral Vision Can Influence Eye Growth and Refractive Development in Infant Monkeys"; Investigative Ophthalmology & Visual Science; vol. 46, No. 11; pp. 3965-3972 (2005).*

(Continued)

*Primary Examiner* — Zachary W Wilkes
(74) *Attorney, Agent, or Firm* — Seyfarth Shaw LLP

(57) ABSTRACT

A method is provided for addressing myopia progression or inclination to myopia in which the influence of accommodative lag stress on myopia is reduced or eliminated to counter eye axial length growth. User depth of focus is increased to relieve stress from overall accommodative effort and stress from accommodation and accommodative lag to retard myopia progression and enable continuous and long tem treatment by the user.

4 Claims, 5 Drawing Sheets

(51) Int. Cl.
  *G02C 7/02* (2006.01)
  *A61F 2/16* (2006.01)
  *A61F 9/00* (2006.01)

(52) U.S. Cl.
  CPC .............. *A61F 2/16* (2013.01); *A61F 2/1618* (2013.01); *A61F 9/00* (2013.01); *A61F 2250/0082* (2013.01); *G02C 2202/24* (2013.01)

(58) Field of Classification Search
  USPC .................................................... 351/159.05
  See application file for complete search history.

(56) References Cited

U.S. PATENT DOCUMENTS

| | | | |
|---|---|---|---|
| 5,796,462 A * | 8/1998 | Roffman | A61F 2/1613 351/159.21 |
| 5,815,236 A | 9/1998 | Vayntraub | |
| 6,045,578 A | 4/2000 | Collins et al. | |
| 6,474,814 B1 * | 11/2002 | Griffin | G02C 7/028 351/159.41 |
| 7,025,460 B2 * | 4/2006 | Smitth | G02C 7/047 351/205 |
| 7,178,918 B2 * | 2/2007 | Griffin | A61F 2/145 351/159.41 |
| 8,876,287 B2 * | 11/2014 | Back et al. | 351/159.12 |
| 2005/0068494 A1 | 3/2005 | Griffin | |
| 2007/0296916 A1 * | 12/2007 | Holden et al. | 351/161 |
| 2008/0084534 A1 * | 4/2008 | Lindacher | A61F 2/1613 351/159.08 |
| 2008/0029139 A1 | 11/2008 | Menezes | |
| 2009/0303442 A1 | 12/2009 | Choo et al. | |
| 2010/0036489 A1 | 2/2010 | Lindacher et al. | |
| 2010/0073629 A1 | 3/2010 | Menezes | |
| 2014/0111763 A1 | 4/2014 | Griffin | |

FOREIGN PATENT DOCUMENTS

| | | |
|---|---|---|
| CN | 101688983 | 3/2010 |
| CN | 102007444 A | 4/2011 |
| EP | 0480748 A | 4/1992 |
| EP | 0996024 A | 4/2000 |
| EP | 1262815 A | 12/2002 |
| EP | 2098192 A1 | 9/2009 |
| JP | 2004526982 A | 9/2004 |
| JP | 2009540373 A | 11/2009 |
| WO | 2000072051 A2 | 11/2000 |
| WO | 2002021194 A2 | 3/2002 |
| WO | 2005055891 A | 6/2005 |
| WO | 2007041796 A | 4/2007 |
| WO | 2007146673 A2 | 12/2007 |
| WO | 20080045847 A2 | 4/2008 |
| WO | 2009129528 A1 | 10/2009 |
| WO | 2011060176 A1 | 5/2011 |
| WO | 2012173891 A1 | 12/2012 |

OTHER PUBLICATIONS

Japanese Patent Office Action, dated Feb. 16, 2016 with English translation; 4 pages.
Williams D R et al. "Off-axis optical quality and retinal sampling in the human eye"; Vision Research, Pergamon Press, Oxford, GB; vol. 36, No. 8, Apr. 1996; pp. 1103-1114.
International Search Report PCT/US2010/056389; dated Aug. 2, 2011; 5 pages.
International Search Report PCT/US 01/28156; dated Aug. 19, 2003; 3 pages.
Intellectual Property Office of Singapore Written Opinion, dated Jul. 31, 2015; 7 pages.
Intellectual Property Office of Singapore Search Report, dated Mar. 4, 2015; 2 pages.
D.G. Green et al., Depth of Focus, Eye Size and Visual Acuity, Vision Research; 1980, vol. 20, pp. 827-835.
Intellectual Property Office of Singapore Written Opinion, dated Mar. 31, 2015; 6 pages.
Intellectual Property Office of Singapore Written Opinion, dated Feb. 11, 2016; 5 pages.
European Patent Office Minutes of the Oral Proceedings before the Examining Division, App. No. 12 728 002.2; dated Mar. 1, 2016; 12 pages.
European Patent Office Decision to Refuse a European Patent Application, dated Apr. 4, 2016; 18 pages.
European Patent Office Summons to Attend Oral Proceedings, dated Oct. 19, 2015; 14 pages.
PCT International Search Report and Written Opinion of the International Searching Authority, PCT/US2012/041621; dated Aug. 21, 2012; 9 pages.
Australian Government Patent Examination Report No. 1, dated Apr. 2, 2015; 7 pages.
Australian Government Patent Examination Report No. 2, dated Jan. 20, 2016; 3 pages.
State Intellectual Property Office of the P.R. China Notification of the First Office Action, dated Feb. 9, 2015 with English translation.
State Intellectual Property Office of the P.R. China the Second Office Action, dated Oct. 13, 2015 with English translation; 11 pages.
State Intellectual Property Office of the P.R. China the Third Office Action, dated Mar. 18, 2016; with English Translation; 14 pages.

* cited by examiner

METHOD OF TREATING MYOPIA PROGRESSIONS

This application is a U.S. National Phase of International Patent Application Serial No. PCT/US2012/041621, filed Jun. 8, 2012, and claims benefit to U.S. Provisional Application Ser. No. 61/497,500 filed Jun. 15, 2011.

BACKGROUND OF THE INVENTION

Myopia or short sightedness is a condition in which the far-point of the eye is less than infinite in distance from the eye. Thus a myopic eye can see objects clearly only within a finite distance, the limit of that far distance moving closer to the eye as the level of myopia increases. Advancing myopia is the result of the scleral ball of the eye elongating (axial myopia) so that the retina that lies against the posterior inner wall of the eye moves behind the eye's distance image focal point. In correcting this condition, a light diverging or "minus" lens must be used to move the focused light from in front of the retina backward to the retinal plane. The minus lens, whether spectacle lens, contact lens or other light diverging ophthalmic appliance, allows the myopic eye to regain the clarity of objects at an infinite distance.

Emmetropization is a process by which the eye continues to develop and grow from birth until full maturity when the process is discontinued. As the eye grows in size, it makes adjustments to both its optical component sizes and its refractive shapes. The adjustments are normally coordinated by chemical processes within the eye so that the eye converges toward the balanced condition known as emmetropia: does not need aids to see clearly at all distances. For reasons not fully understood, emmetropization does not always proceed as it should, leaving the eye myopic (and usually progressively so) or, less often, hyperopic.

It has been hypothesized that the development of the eye refractive state is driven by many interacting influences including the eye shape, retinal light patterns, and the nature of visual stimuli experienced. Additionally, individual differences in eye shape and its peripheral refractive condition that are integrated to initiate a chemical growth signal, all determine the direction of emmetropization. Therefore, we are able to assess certain clinically observable factors.

For close work and reading (in young healthy eyes), the mechanism of the crystalline lens and ciliary muscles increase the crystalline lens power to focus objects that are closer than infinity. The term "accommodation" is used to indicate this action of eye's internal optics to create a more focused image on the retina. Accommodation involves use of internal ciliary muscles and external muscles that further increases stress to the eyeball itself. Therefore, aspects of accommodation itself are believed to increase risk of myopic development. Accommodative lag is an ocular anomaly found usually in myopic subjects wherein the eyes lag behind the near focus of an object of regard such as reading print. Accommodative lag has been shown to be a risk factor in inducing myopia.

Myopia typically begins with certain discernable but often nebulous symptoms that are sometimes referred to as "prodromal symptoms of myopia" or "school myopia". Frontal headache, transient blurred vision both near and far, and difficulty reading are symptoms of accommodative stress and beginning myopia in young school children. Nearwork-induced transient myopia (NITM) is found usually in older students and adults, but presents similarly. An overall descriptor of these two similar but separate conditions is the term pseudomyopia. Pseudomyopia is an intermittent, temporary shift in refraction of the eye toward myopia, in which the focusing of light in front of the retina is due to a transient spasm of the ciliary body or muscle group. This in turn causes a temporary increase in refractive power of the eye. A user perceived result is impaired distance vision. It is believed by most eye-care practitioners that NITM is another major risk factor that connects nearwork-related symptoms to the development of permanent myopia.

Inherently, myopia control involves relatively youthful eyes and, when designing or prescribing optical appliances such as contact lenses or spectacles, the particular issues and needs of the young must be addressed if myopia is to be successfully thwarted. Young users of corrective lenses have been found to demonstrate a high degree of sensitivity to any form of optical distraction. This has been illustrated by their difficulty in maintaining use of progressive power spectacle lenses with any great amount of power variation. Also, optical defects such as diffraction from optical discontinuities such as those in traditional bifocal lenses are a source of particular discomfort and prevent long-term use by many young users. Further, due to the extended periods of close work experienced by many school age youth, accommodation and accommodative stress is a source of discomfort that may sometimes limit use of corrective lenses by the young.

While many optical methods and devices have been proposed in the prior art for remedying myopia or myopia progression, all suffer from some aspect that prevents long-term use by the young. Unless the treatment method or device can be comfortably and reliably used by young persons, myopia control is not practicable. The result is that no real solution is available to address myopia. What is needed is an optical lens and method of treatment that counteracts the risk factors associated with myopia progression including accommodative stress, NITM and related pseudomyopia and at the same time addresses the particular needs of the young person so that a successful result can be obtained.

SUMMARY OF THE INVENTION

The invention provides a method of addressing myopia progression or inclination to myopia in which the influence of accommodation and accommodative lag stress on myopia is reduced or eliminated to counter eye axial length growth. These effects are critically provided in a form that is acceptable to the user in a manner to enable continuous and long term treatment.

The invention provides a method of retarding or halting progression of myopia in which an optical system is provided to enable clear distance vision in the foveal area of the retina. Depth of focus is increased to relieve stress from accommodation and accommodative lag to retard myopia progression and enable continuous and long term treatment by the user.

Optical devices according to the invention include a small central zone of clear vision where the refractive power rises slowly yet continuously from a central power to a limit of clear vision. This central zone is surrounded by a more rapidly increasing power distribution generating a perceivable blur to the user that causes an attendant increase in effective depth of focus. By increasing the depth of focus, the eye's accommodation is more relaxed and accommodative stress is reduced as well as any influence on myopia progression. Simultaneously, there is an increase in depth of field that allows objects to be positioned closer to the eye without requiring muscular contraction within the eye's focusing mechanism. The increased depth of focus and depth of field afforded by the present invention not only allows for clear comfortable vision, but relieves the forces that push the eye into myopia.

Although the present device is not a physical pinhole and nor does it resemble a pinhole, it produces similar increased depth of focus effects to the user. However, the present invention does not suffer from the loss of light and increased diffraction inherent in physical pinholes. The present device increases the depth of field and depth of focus by reducing the size of the entering "pencil" of light using a favorable power distribution, and without blocking the light reaching the image plane or retina. Additionally, the lag of accommodation seen in most prodromal myopic cases is corrected by the present invention by virtue of its greater depth of focus and depth of field. Accommodative lag in potential users is usually found to be between 0.25 and 2.00 diopters, which is well within the capabilities of the present invention.

It is important to the efficacy of the present invention that the causation of the increased depth of focus, namely the smooth and continuous large rise in focal power, be undiscovered by the visual cortex of the lens wearer. Abrupt surface or power changes make adaptation to lenses difficult for the wearer.

The methods and designs provided here are applicable to all conventional lenses used to treat vision in persons including contact lenses, intraocular lenses, and spectacle lenses.

Additional novel aspects and benefits of the invention will be discerned from the following description of particular embodiments and the accompanying figures. The scope of the invention is not intended to be limited to the above summary nor the below examples, but includes configurations and embodiments including the same inventive aspects as claimed.

DETAILED DESCRIPTION OF EMBODIMENTS OF THE INVENTION

An optical appliance such as a lens according to the present invention includes a continuous axi-symmetric power distribution that provides multiple coordinated functions. A central portion of the lens has a power distribution selected preferably for correcting a user's distance vision. Surrounding the distance corrective power the power distribution increases in power quickly over a short radial dimension to produce a blur effect on the user's vision. This radial area of rapidly rising power is termed here for convenience a "blur" zone. In the present invention, the magnitude of blur in the blur zone that encircles the clear zone is chosen so that the eye cannot resolve a selected level of detail in the distance. This simulation of a small hole generates an increased depth of focus due in part to the user's cortical response to the blur of inhibition and, it is believed, some level of vision enhancement due to the phenomenon known as "simultaneous blur contrast". There is an effective reduction in the aperture of the eye with an associated increased depth of focus. By properly specifying the distance vision power to the particular user, the associated increased depth of focus of the lens will compensate, at least partially, for accommodative lag occurring when the user attempts near vision. This compensatory or "pseudo" accommodation provides clearer vision and reduced accommodation stress and accommodative lag stress that are believed to be associated with myopia progression.

Figure 1:
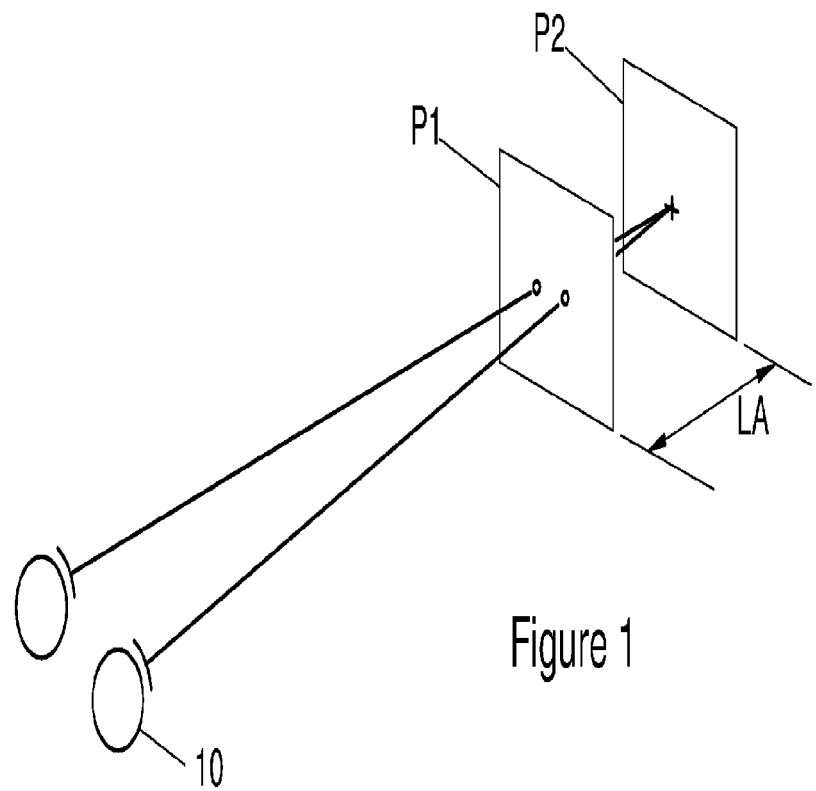
FIG. 1 is an illustration the concept of "accommodation lag" as used respecting the invention.

FIG. 1 depicts the relation of an optical plane of regard P2 and an object plane P1 (intended or desired plane of regard) respecting a viewer's eyes 10 attempting to focus on an object in the object plane P1 at a distance less than infinite from the viewer. The viewer attempts to focus both eyes on the object. To do so, each eye must alter its optical (neuro-muscular) mechanism—accommodate—to alter the eye's optics appropriately. However, the eye's failure to fully accommodate results in the eyes focusing on the (actual) optical plane of regard P2. The dimension LA that is the difference between the intended object plane P1 and the farther optical plane of regard P2 is known as the lag of accommodation. This difference may also be represented in terms of the difference in optical power required to bring objects at the two planes into focus on the retina. While both of the viewer's eyes are depicted in the illustration for clarity, the lag of accommodation exists independently in each eye.

So long as the lag of accommodation exists, the viewer will experience stress in various forms produced by the ongoing effort to accommodate and from the cortical signals resulting from the perceived out-of-focus image at the retina.

Figure 2:
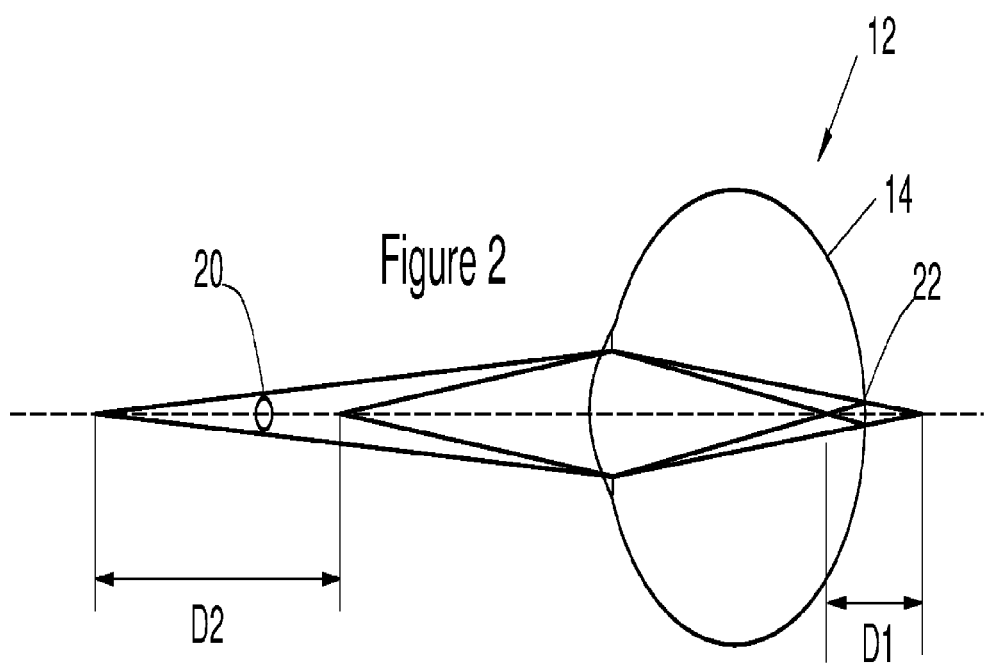
FIG. 2 is an illustration of the depth of focus and depth of field concepts as used respecting the invention.

FIG. 2 illustrates the concepts of "depth of field" and "depth of focus" and are shown here to clarify the application of the concepts in the present invention. The depth of focus D1 and depth of field D2 are shown respecting the optical system of an eye 12 and its retina 14. The depth of focus D1 is the dimension over which a focused image is perceived. That is, within the depth of focus D1, the perceived clarity of the image is effectively the same. At distances closer or farther from the optical system (outside the depth of focus), any image is effectively unfocused. Depth of field D2 refers to a dimension, respecting the object viewed, in which an object creates an image within the field of the depth of focus, and is therefore focused. The depth of focus D1 and depth of field D2 for any optical system is dependent on a variety of optical system characteristics.

From this it can be understood that for any particular condition of the eye 12 wherein a distant object may be focused on the eye retina 14, there is a range of other distances from the eye (defined by the depth of field D2) in which the object will be equally in focus to the viewer.

In circumstances where an object 20 is in focus on the retina 14, and is then moved in toward the eye 12, the accommodative mechanism of the eye remains relaxed so long as the object 20 remains in the depth of field D2. Once the object leaves the depth of field, and the image 22 on the retina 14 begins to be perceived as blurred, the accommodative system responds and ciliary body in the eye flexes its smooth muscle cluster to cause the lens to flex within the eye. Where the depth of field D2 (and depth of focus D1) can be increased, the range of distances in which the accommodation mechanism will remain relaxed is also increased. This phenomenon can be considered free accommodation or "pseudo-accommodation" as it represents an accommodation to the change in the object distance that the eye does not have to provide to maintain a focused image.

Figure 3:
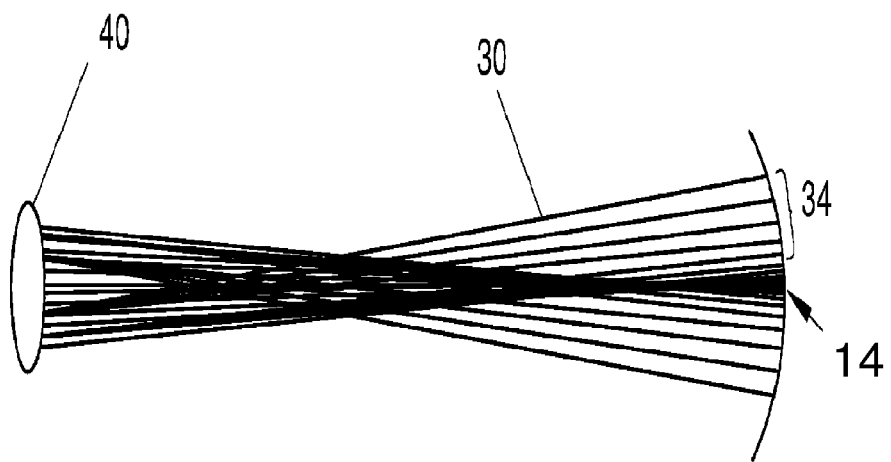
FIG. 3 is an elongated caustic resulting from a lens according to the invention.
Figure 5:
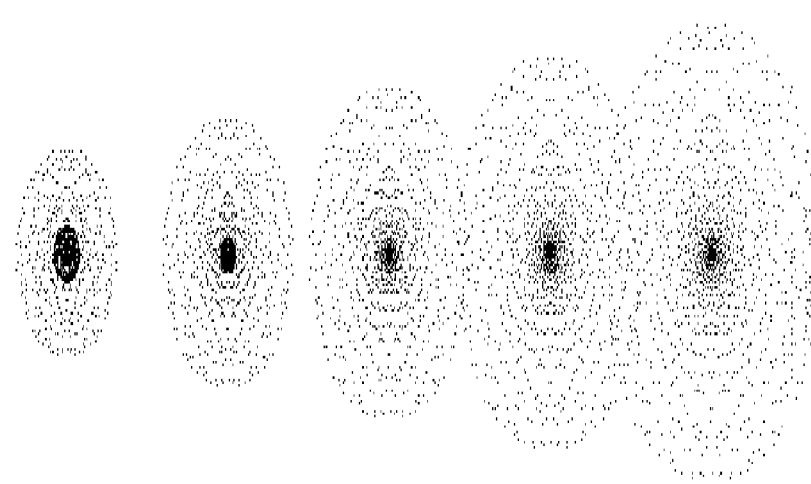
FIG. 5 is a series of spot diagrams taken from a caustic of a lens according to the invention.

FIGS. 3 and 5 illustrate the optical effect of the blur zone and power distribution of the present invention. FIG. 3 is the elongated caustic resulting from a lens according to the invention. Representative rays 30 are shown as passing through a lens 40 and impinging on a retina 14. Due to the influence of the lens power distribution, a dense central focus occurs at the center of the retina 14, in the fovea. A consequence of the blur power and lens peripheral power distribution is a sparse light ray fan 34 outside the dense center of the caustic. This impinges on the retina 14 peripherally from the central retina. This unfocused light is inhibited from perception or recognition by the user's visual cortex; the result being increased clarity of the image received by the fovea. This inhibitory aspect results in further increased effective depth of focus.

Figure 4:
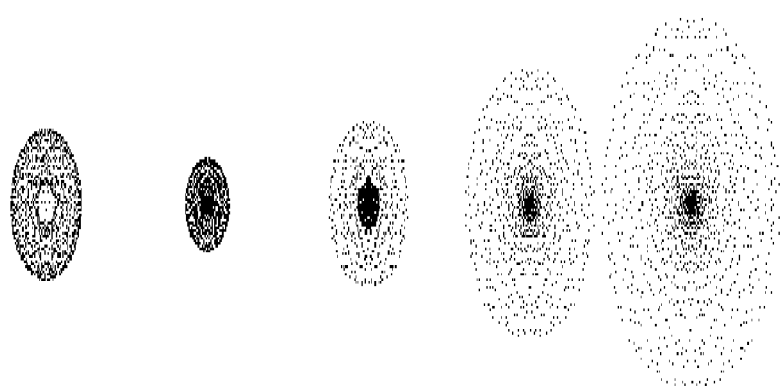
FIG. 4 is a series of spot diagrams taken from a caustic of a conventional single power prior art lens.

FIG. 5 is series of spot diagrams respecting the caustic of FIG. 3. FIG. 4 is a spot diagram series respecting a caustic for a conventional spherical single power lens that is provided for comparison. Each series, from left to right, are at increasing distance from the lens towards the retina. The increased depth of focus for the inventive lens in FIG. 5 is illustrated by the relatively high density at the center in all of the diagrams for the inventive lens. The outer area of thinly spaced spots surrounding the center focus at the retina for the spherical lens in FIG. 4 are due to spherical aberration from an imperfect lens construction.

Figure 6:
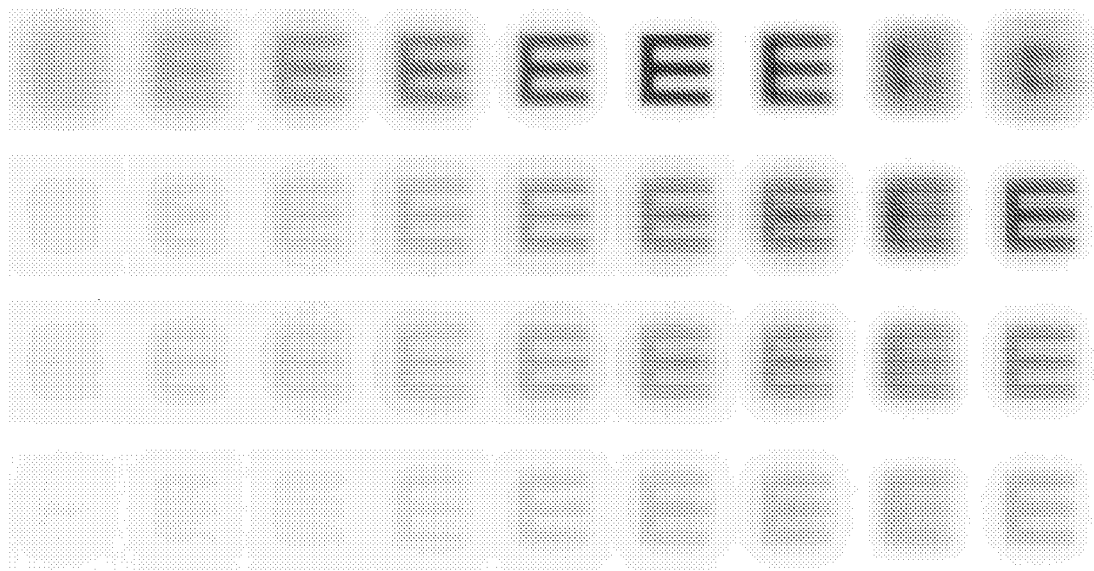
FIG. 6 is a series of "E" chart images resulting from the analysis of light passing through a lens according to the invention.
Figure 7:
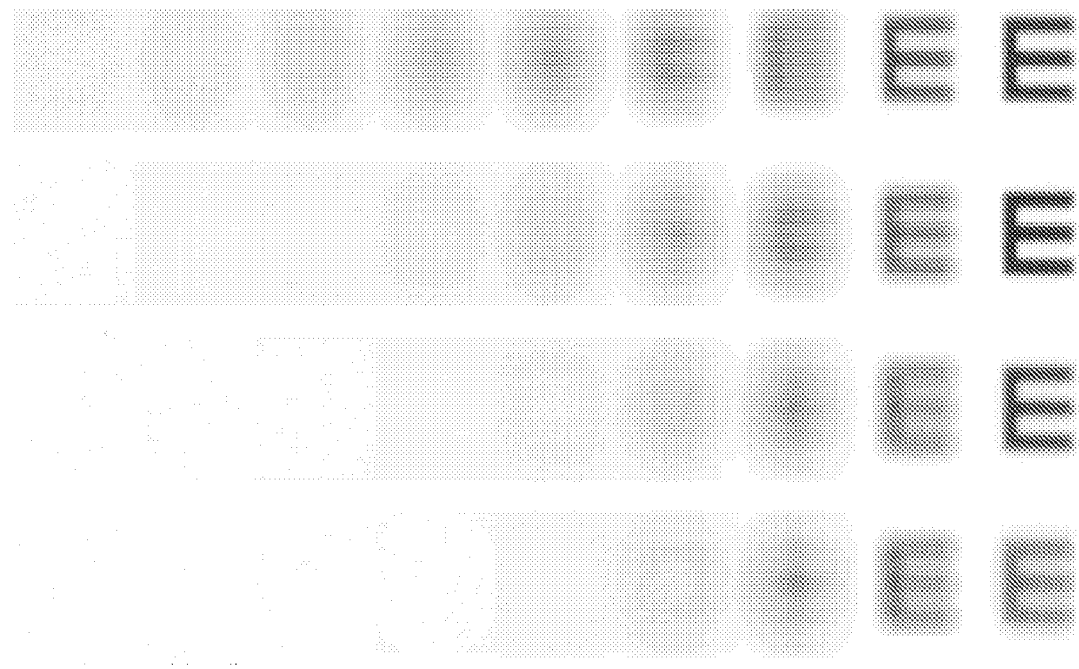
FIG. 7 is series of "E" chart images resulting from the analysis of light passing through a single power conventional lens of the prior art.

The consequences of the increased depth of focus and peripheral ray fan are in part illustrated in the "E" charts found in FIGS. 6 and 7. The charts are produced by analysis using the well known Zemax™ optical system computer program. FIG. 6 represents the analysis of a lens according to the invention on an eye with various pupil sizes and at a range of object distances from the eye: from 25 centimeters (left) to infinity (right). FIG. 7 is the result of similar analysis of a spherical lens with the same apical power as in the lens producing the results of FIG. 6, and with the same pupil sizes and distances. Inspection indicates that the inventive lens provides a discernable image through an increased range distance (depth of field). In comparison, the spherical lens used to produce the results of FIG. 7 does not provide a discernable image except at infinity and relatively far distances (the right most of the series). The result is insufficient image detail for resolution by the user's vision system at other distances for the spherical lens. Resolvable images are available with the inventive lens at a greater range of distances than with a spherical single power lens. For this reason, an inventive lens with appropriate distance corrective power will require less accommodation by the user's eye to bring a near object into effective focus. Relative performance or effectiveness of a lens or lenses can be evaluated in this manner by empirical comparison of associated "E" charts, or similar representations of images produced by the optical devices. Alternatively, specific depth of focus data can be obtained for a subject lens or lenses by other known analytical methods and devices for the comparison and evaluation purposes here.

While the above effects are similar to that produced by optical apertures, no physical aperture with an obscuring border is involved in the present invention.

Figure 8:
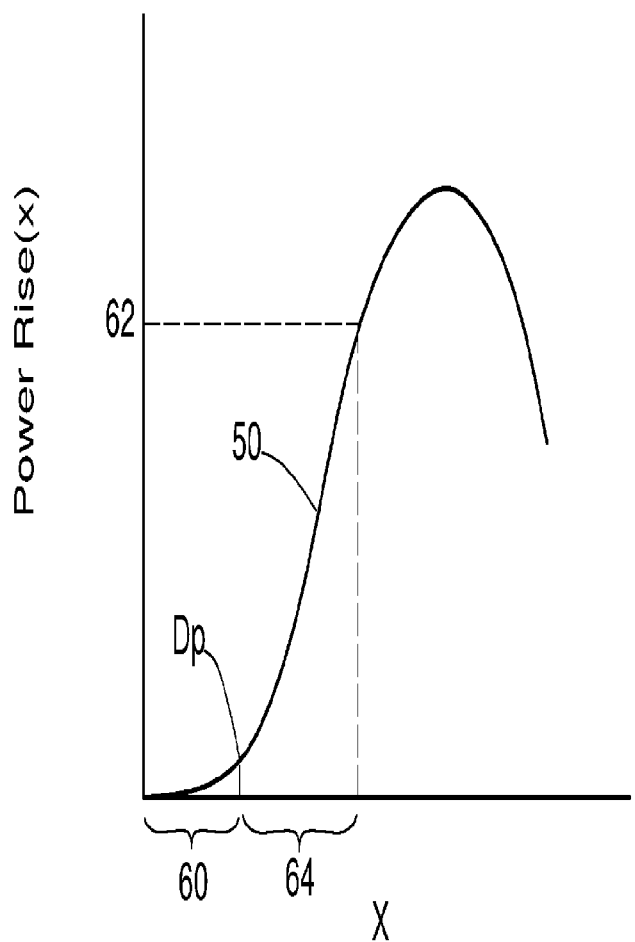
FIG. 8 is a plot of the radial power distribution for embodiments of a lens according to the invention.

FIG. 8 depicts a graph of the distribution 50 of the optical power rise as a function of radial dimension (x) from the apex of a lens according to the invention. The power rise is the power above the distance corrective power (apical power). A centrally located distance vision region 60 has a power distribution that varies within a power range that is effective with the apical power for distance vision correction. The distance correction power is that power providing clear vision when viewing objects infinitely distant from the user. The required distance correction power may vary with the specific requirements of the user. The distribution power rise initially increases continuously but slowly with increasing radius to provide an effective area for distance power needed. This continues to a design point DP at a radial dimension in the range of about 0.5 to 1.5 millimeters from the apex. Maintaining a radial location at or outside the minimum is preferred to provide sufficiently clear distance vision for most users in full and low light conditions. Constraining the radial dimension to at or below the upper end of the range is necessary to provide the needed increase in depth of focus. The power rise at the design point is preferably in the range of +0.5 to +0.75 diopters, but may be as high as +1 diopter for some designs. At powers above this, most users are likely to perceive blur in distance vision; as well the distance vision may have insufficient contrast in low light conditions.

Beyond the design point DP, the power increases more quickly and continuously until a maximum power value 62 is reached. The portion of the lens and power distribution 50 between the design point DP and peak power 62 defines and creates a blur zone 64. The rapidly rising power in the blur zone 64 produces in the user the unfocused light impinging peripherally on the retina as discussed above. It is critical that immediately outside the design point DP, the power distribution rises sufficiently quickly to both ensure the result of blur vision induced in the user during distance vision, and that the desired and necessary maximum be reached within the constraint of the pupillary dimension. The maximum may be defined by the power distribution relationship itself or may be a result of the power distribution being terminated by construction of the lens. For example, beyond the radial dimension of the peak power, a contact lens may be blended into a constant power in a conventional lens carrier portion. In FIG. 8, the power distribution 50 is shown to continue beyond the peak power to illustrate that the power distribution 50 may be defined as a portion of a continuous power relationship. In this figure and the below equations, the optical power discussed is particularly the tangential power, which may be somewhat different from the sagittal power or average power at any point on a lens. This relationship will be understood and particular lens designs may be approached entirely using the tangential powers defined here. At the same time, inspection of a lens may involve measurement of sagittal power or the average of tangential and sagittal powers. Where an optical system includes other optically effective elements, such as for example the posterior surface of a contact lens (on the eye or in air or other medium) the optical power of those elements must be used to adjust the desired powers to obtain a surface power distribution for the purposes of defining an anterior surface according to the equations herein.

As discussed with respect to FIG. 6, the produced blur is actually inhibited or suppressed by the user's optical cortical system and the blur is not recognized by the user. This is, however, dependent on the lack of any distracting diffractive aspects in the optical system as discussed before.

The power rise above the design point must be substantially greater than the apical power to produce the desired increased depth of focus. Preferably the peak power rise 62 is in the range of +1 to +10 diopters for contact lenses. However, for some users, effective increase in depth of focus may be provided by lower peak powers. The upper limit of the range is controlled in practice by the subjective tolerance of users to the blur effect in long term use. The appropriate peak power value may be dependent on the particulars of the user, for example the age of the user and their required distance correction as well as other factors. With contact lenses using the above parameters, decreases of accommodative lag, from increased depth of focus, in the range of +0.25 to +2 diopters are possible. The appropriate peak power for other forms of refractive lenses may be greater or less depending on their nature. In some applications, peak power may be as great as 100 or more.

The average human eye has a depth of focus of about +0.5 diopters or less. Typically, +0.25 of increased depth of focus will be effective to counter accommodative lag in typical users. An increase of +0.25 to +1.0 diopters in depth of focus is suggested as effective to remedy expected accommodative lag and also provide additional "pseudo" accommodation sufficient to treat ongoing myopia progression or prevent or slow the onset of myopia.

An effective front surface power distribution can be generated by the following power exemplary equation for power rise for a rotationally symmetric lens system (a spherical, aspherical, or toric base curve must be added to the total power):

$$\text{Power}(x) = 10^3 \cdot (n-1) \cdot \left( \frac{1}{R(x)} - \frac{1}{r} \right) \qquad \text{Eq. 1}$$

Where:
Power(x) is the power rise above the apical power,
x is the radial distance from the center,
n is the refractive index of the optical device material,
r is the radius of curvature at the apex (center),
R(x) is the radius of curvature as a function x as given below in Eq. 2

$$R(x) = \frac{[1 - (z'(x))^2]^{1.5}}{z''(x)} \qquad \text{Eq. 2}$$

Where:
z'(x) and z''(x) are the first and second derivative, respectively, of the function z(x) given below in Equation 3 in the form of the power function:

$$z(x) = \frac{[(Z)^{x/r} + (Z)^{-x/r}] - 2}{\frac{2}{r} - \ln(Z)^2} \qquad \text{Eq. 3}$$

Where:
Z is a form factor with a value in the range of 1 to 100.
Equation 3 defines z(x) which is a sagittal depth dimension of an optical surface such as the anterior surface of a contact lens. The shape defined by z(x) is applied as a surface of revolution about the apex to provide the associated desired power distribution. The apical radius of curvature (r) may be defined in the conventional manner by the particular target user eye geometry, the lens material properties, and the distance vision correction required.

The form factor Z provides a means to adjust the shape of the power distribution and maximum power peak to satisfy particular requirements. Selection of a most appropriate value of Z, to result in the desired power form and peak power, may be accomplished by trial and error iteration, that experience indicates will quickly convergence on the desired result. While value in the range of 1 to 100 will be preferred in many instances, Z may have a value of any positive number.

As shown above, the depth of focus of a particular optical system can be represented by graphical representation such as the optical analysis output in "E" chart image form. Improved depth of focus can be achieved by iterative and, or, comparative analysis of different power distributions by examination of "E" charts or like representation of depth of focus for each power distribution, followed by appropriate selection. Such analysis is preferably performed on the basis of the light paths through the entire optical system, including the user's eye and any applied lens.

In contact lenses, the power distribution (and surface shape) may be applied to whatever radial extent necessary and then blended smoothly into a peripheral corrective region or a surrounding carrier. The above equations may be applied using numerical methods and may be reduced to digital forms or tabulated. Other mathematical forms and relationships and equations exist and are contemplated to provide similar power distributions with the required characteristics herein specified. The above Equations 1 to 3 provide only one such alternative and are not limiting. For example, alternative forms of an effective optical surface may be provided by variations of what is known as the universal optical equation.

The above Equations 1 to 3 provide only one such alternative and are not limiting. For example, alternative forms of an effective optical surface may be provided by variations of what is known as the universal optical equation. Another form of the universal optical equation can be expressed as in Equation 4:

$$z(x) = \frac{x^2/r}{1 + \sqrt{1 - S(x/r)^2}} + ax^3 + bx^4 + cx^5 + \ldots mx^n \qquad \text{Eq. 4}$$

where S is the shape factor and r is the apical radius while the coefficients a, b, c, etc. may be determined empirically as discussed above to provide a lens shape and corresponding power distribution performing the desired inventive function. Equation 4 may then be applied in above Equations 1 and 2 to obtain an instantaneous power profile.

EXPERIMENTAL TESTING. The efficacy of the present methods and devices in treating myopia and myopia progression was tested by experimentation with young live chicken subjects. For a variety of known reasons, chick studies have been used by others in the past to test and study optical appliances and methods and the results accepted as relevant in predictions of human results.

Evidence has indicated that newly hatched chickens fitted with minus power lenses demonstrate a myopic shift approximately equal to the lens power. A chick study was completed to determine if lens-induced myopia in chickens can be inhibited by a lens of the inventive design having a central minus power combined with the increased depth of focus power distribution of the present invention.

Methods: Fifteen young chicks were used in the test. Each was fitted unilaterally with a lens, made in PMMA, and attached by Velcro™ in close proximity to the chick's eye. Eight of the fifteen chicks were fitted with a test lens according to the present invention and having with central power of −10.00 D. A relatively high power level was used as a consequence of scaling for the optical size of the chicks eyes and are proportional in effect to lower powers used for humans. The remaining seven chicks (control group) were fitted with a conventional spheric lens of the exact same physical parameters as the test lens and also having −10.00 D central power. For each chick, the eye fitted with a lens is considered the treated eye.

The chicks were given food and water ad libitum and raised on 14/10 hour light/dark cycles. The applied lenses were removed only for brief periods for measurements and lens cleaning. Refractive error in both eyes of each chick was measured by retinoscopy before lens application (day zero) and at days 3 and 7 (after application). The mean differences (Mdiff) in refractive error between the treated and untreated eyes were calculated.

Results: The differences between the refractive error of the treated and the non-treated eyes was insignificant (p=1.00) on day zero for both groups. For the Test group MDiff was −0.06 D (±0.50), while the error absolute values ranged from +1.00 to −0.50 D. For the control group the MDiff was +0.29 D±0.76 with a value range of +1.00 to −1.00 D.

By day 7 of the study, chicks treated with the test lenses had become slightly hyperopic in the treated eye relative to the untreated eye with MDiff +2.17 D±2.71 (p=0.32) and a range of +6.00 to −1.00 D. At this time-point those treated with the conventional spheric control lenses had become significantly more myopic (p<0.0007, Tukey) in the treated eye relative to the untreated eye (MDiff −8.10 D±3.07; range −5.00 to −12.00 D). The MDiff for the test and control groups were significantly different at day 7 (p=0.0002, Tukey).

The results of this short-term study indicate that lens-induced myopia in chickens can be affected by the inventive lens design and by the current methods of treatment. It is important to note that the center region of test lenses has the same power as the control lens (single uniform power), differing only in the distribution of the power peripherally to the central area. Consequently, it can be said that the eyes of test chicks wearing the test lens experienced the same optical stimulation from the central portion of the lens worn as did the control chick. The difference, resulting in the differences in eye growth response, can be said to be from the lens form peripheral to the central power.

It is critical that any lens in continuous use by a youthful person in particular subject the user with no diffractive optical effects and preferably include no extreme power changes. This is due to the observed high sensitivity of young persons to these optical aspects. Continuous use of the treatment lens during vision is important to efficacy in addressing myopia and myopia progression. Consequently, the lenses here must provide optically smooth surfaces and power distributions.

While the above exemplary embodiments regard contact lenses, the same concepts and methods may be applied to other refractive optical devices such as IOLs, and methods of altering a person's optical tissues such as surgical methods, as well as other like devices and methods for the same purposes. In other lens forms, both the design point location and power and peak power magnitude will differ from the examples given here. However, the same results can be provided from the same form and characteristics of the power distribution. Spectacles and diameters of lenses worn in front of the eye and designed using the present invention must be scaled upward in size to an appropriate diametric dimension of from about 20 to 100 mm and must be adjusted for the vertex power change outward for 10 to 20 millimeters in front of the eye.

If an inventive lens is defined in equation form, the first and second derivatives of the power distribution should be continuous to satisfy the requirement of a smooth distribution. Lenses may be defined by other means, such as by digitized surface contours, and satisfy the smooth requirement if the resulting lens power may be described by one or more power distribution relationships with continuous first and second derivatives or if the power distribution otherwise provides the same functional result.

The preceding discussion is provided for example only. Other variations of the claimed inventive concepts will be obvious to those skilled in the art. Adaptation or incorporation of known alternative devices and materials, present and future is also contemplated. The intended scope of the invention is defined by the following claims.

The invention claimed is:

1. A method for treating myopia and myopic progression, comprising the steps of:
   determining a user has myopia;
   providing a lens having a central region about an apex of the lens that yields clear distance vision, and an optical blur region immediately surrounding the central region that yields an unfocused optical image; and
   positioning the lens on an eye of a user to provide an induced aperture and an increased depth of focus when used to correct vision of the user, relative to when the lens is not positioned on the eye of the user,
   wherein the central region includes an optical surface creating a power distribution that varies smoothly from an apical power at a central point on the apex designed for distance correction through increasing power immediately surrounding the central point to inhibit or reduce myopic progression in the eye, relative to when the lens is not positioned on the eye of the user.

2. The method of claim 1 wherein the lens, when positioned on the eye of the user, enables relief of accommodative stress in the eye, relative to when the lens is not used.

3. The method of claim 2, wherein the depth of focus is within +0.25 to +1.00 diopters.

4. The method of claim 2, wherein the user has a reduction in accommodative lag of about +0.25 to about +1.00 diopters relative to when the lens is not positioned on the eye of the user.

* * * * *